US006656217B1

(12) United States Patent
Herzog, Jr. et al.

(10) Patent No.: US 6,656,217 B1
(45) Date of Patent: *Dec. 2, 2003

(54) MEDICAL DEVICE COATED WITH A POLYMER CONTAINING A NITRIC OXIDE RELEASING ORGANOMETALLIC NITROSYL COMPOUND USEFUL FOR THE PREVENTION OF PLATELET AGGREGATION

(75) Inventors: William R. Herzog, Jr., Baltimore, MD (US); Sovitj Pou, Baltimore, MD (US); Gerald M. Rosen, Lutherville, MD (US); Yi-Ju Zhao, Baltimore, MD (US)

(73) Assignee: NovoVascular, Inc., Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 09/254,002

(22) PCT Filed: Aug. 27, 1997

(86) PCT No.: PCT/US97/15022

§ 371 (c)(1),
(2), (4) Date: Dec. 2, 1999

(87) PCT Pub. No.: WO98/08482

PCT Pub. Date: Mar. 5, 1998

Related U.S. Application Data

(63) Continuation-in-part of application No. 08/703,646, filed on Aug. 27, 1996, now Pat. No. 5,797,877.

(51) Int. Cl.$^7$ .................................................. A61F 2/06
(52) U.S. Cl. ................. 623/1.15; 623/1.43; 623/23.71; 623/926; 604/266
(58) Field of Search ................................ 604/265, 266; 623/1.15, 1.43, 11.11, 903, 926, 23.71

(56) References Cited

U.S. PATENT DOCUMENTS 5,207,706 A * 5/1993 Menaker ........................ 623/1
5,405,919 A * 4/1995 Keefer et al. ................ 525/377

(List continued on next page.)

OTHER PUBLICATIONS

"Commentary—Signal Transduction Mechanisms Involving Nitric Oxide," by Louis J. Ignarro, *Biochemical Pharmacology*, vol. 41, No. 4, pp. 485–490, 1991. (Printed in Great Britain).

(List continued on next page.)

*Primary Examiner*—Paul B. Prebllic
(74) *Attorney, Agent, or Firm*—Venable LLP; Michael A. Gollin; Keith G. Haddaway

(57) ABSTRACT

The aggregation of platelets on the surface of a foreign body exposed to the flowing blood of a living being (such as plastic tubing, a balloon or the end of a catheter surgically inserted in a blood vessel, a stent implanted therein or synthetic grafts, which surface normal promotes such platelet aggregation to form a coating firmly affixed to that surface which would restrict the flow of blood past that surface or to form a blood clot detachable from that surface), is inhibited by a gas permeable coating on the surface of a physiologically acceptable polymer as which contains dissolved or dispersed therein a nitrosyl-containing organometallic compound, such as sodium nitroprusside, which is protected from diffusion from the coating and from direct contact with the blood and which slowly decomposes at the body temperature within the coating and in so doing releases a platelet aggregation-inhibiting amount of nitric oxide which diffuses from the coating during the period when platelet aggregation by the surface of the foreign body would be promoted in the absence of the polymer coating.

28 Claims, 2 Drawing Sheets

U.S. PATENT DOCUMENTS

| | | | | | |
|---|---|---|---|---|---|
| 5,470,307 | A | * | 11/1995 | Lindall | 604/20 |
| 5,536,241 | A | * | 7/1996 | Zapol | 604/23 |
| 5,599,352 | A | | 2/1997 | Dinh et al. | |
| 5,605,696 | A | | 2/1997 | Eury et al. | |
| 5,665,077 | A | * | 9/1997 | Rosen et al. | 604/266 |
| 5,797,887 | A | * | 8/1998 | Rosen et al. | 604/265 |
| 6,087,479 | A | * | 7/2000 | Stamler et al. | 530/363 |
| 6,255,277 | B1 | * | 7/2001 | Stamler et al. | 514/2 |
| 6,379,691 | B1 | * | 4/2002 | Tedeschi et al. | 424/423 |

OTHER PUBLICATIONS

"Photochemistry of Pentacyanonitrosylferrate (2–), Nitroprusside," by Steven K. Wolfe and James H. Swinehart, *Inorganic Chemistry*, vol. 14, No. 5, pp. 1049–1053, 1975.

"Nitric Oxide—A Simple Molecule with Complex Biologic Functions," in *Free Radicals—Biology and Detection by Spin Trapping* by Gerald M. Rosen, Bradly E. Britigan, Howard J. Halpern and Sovitj Pou,, pp. 83–139, 1999.

* cited by examiner

MEDICAL DEVICE COATED WITH A POLYMER CONTAINING A NITRIC OXIDE RELEASING ORGANOMETALLIC NITROSYL COMPOUND USEFUL FOR THE PREVENTION OF PLATELET AGGREGATION

This application is a National Stage Application of PCT Application No. PCT/US97/15022, filed Aug. 27, 1997, which claims the priority and is a continuation-in-part of U.S. application Ser. No. 08/703,646, filed Aug. 27, 1996, now U.S. Pat. No. 5,797,887.

BACKGROUND OF THE INVENTION

1. Field of the Invention

This invention relates generally to novel drug delivery systems containing a nitric oxide-releasing metal compound entrapped therein and methods for using them, more particularly for the inhibition of restenosis after percutaneous transluminal coronary angioplasty and for the inhibition of acute or subacute thrombotic occlusion related to the use or deployment of a synthetic device within the vascular tree or extracorporeally.

2. Description of the Prior Art

Sodium nitroprusside (SNP) and similar nitrosyl-containing organometallic compounds, whether ionic salts or chelates, which can release nitric oxide (NO), have been known since the mid-1950's to exhibit short-term hypotensive effects. The mechanism by-which this drug elicited its pharmacological activity was not known until the discovery that endothelial cells secreted a factor, which regulated vascular tone, termed Endothelial-Derived Relaxation Factor (EDRF) (Furchgott and Zawadzki, *Nature*, 288: 373–376, 1980). In 1987, Palmer and coworkers (*Nature*, 327: 524–526, 1987) determined that the free radical nitric oxide mimicked many of the physiologic properties reported for EDRF. Besides regulating vascular tone, nitric oxide has been found to control a wide variety of physiologic functions, including (a) inhibition of neutrophil adhesion (Kubes, et al., *Proc. Natl. Acad. Sci. USA*, 88:4651–4655, 1991), (b) enhancement of macrophage-mediated microbial killing (De Groote and Fang, *Clin. Infect. Dis.* 12 (Suppl 2): S162–S165, 1995) (c) amelioration of impotence (Burnett, et al., *Science*, 257: 401–403, 1992) and (d) regulation of various CNS functions (Dawson, et al., *Ann. Neurol.* 32: 297–311, 1992). Of relevance to this invention are those studies demonstrating that nitric oxide inhibits platelet aggregation (Furlong, et al., *Brit. J Pharmacol.* 90: 687–692, 1987; Radomski, et al., *Lancet, ii*, 1057–1058, 1987) and prevents restenosis (McNamara, et al., *Biochem. Biophys. Res. Commun.* 193: 291–296, 1993).

Since nitric oxide regulates many physiologic functions, this free radical is an essential ingredient for maintaining normal life processes. However, pharmacological applications of nitric oxide are limited, since systemic use can result in severe toxicity. For instance, administration of gaseous nitric oxide systemically to treat localized abnormalities or diseases is impractical except in a hospital intensive care setting, because control of its dosage in the therapeutic range cannot easily be achieved. Even if it were possible to carefully titrate the gaseous dose of nitric oxide to minimize systemic toxicity, it would be very difficult to locally administer this drug to sites of interest. Therefore, the development of therapeutic agents, which would mimic the pharmacological action of nitric oxide, has received considerable attention. Several classes of nitric oxide-releasing compounds have been developed, including syndnoeimine (Noack and Feelisch, *J. Cardiovasc. Pharmacol.* 14S: 51–55, 1989), nitroglycerin (Noack and Feelisch, *J. Cardiovasc. Pharmacol.* 14S: 51–55, 1989), S-nitroso derivatives (Ignarro, Lippton, Edwards, Baribos, Hyman, Kadowitz and Gretter, *J. Pharmacol. Exp. Ther.* 218: 729–739, 1981; Kowaluk and Fung, *J Pharmacol. Exp. Ther.* 255: 1254–1256, 1990; Stamler, Loscalzo, Slivka, Simon, Brown and Drazen, U.S. Pat. No. 5,380,758, 1995) and N-nitroso compounds (Maragos, Morley, Wink, Dunams, Saavedra, Hoffman, Bove, Issac, Hrabie and Keefer, *J. Med Chem.* 34: 3242–3247, 1991; Keefer, Dunans and Saavedra, U.S. Pat. No. 5,366,997, 1994, Keefer and Hrabie, U.S. Pat. No. 5,405,919, 1995; Keefer, Hrabie and Saavedra, U.S. Pat. No. 5,525,357, 1996). These compounds require either hydrolysis or metabolic activation, through either oxidation or reduction, to generate nitric oxide. Alternatively, several studies have reported on the development of photolyzed "caged-nitric oxide" compounds. For example, the organometallic compound sodium nitroprusside has been found to release nitric oxide upon light activation (Bates, Baker, Guerra and Harrison, *Biochem. Pharmacol.* 42S: S157–S165, 1991). Contrary to this, nitric oxide generation from light activation of ruthenium nitrosyl trichloride failed to inhibit platelet aggregation, thereby questioning the utility of this approach (Makings and Tsien, *J. Biol. Chem.* 269: 6282–6285, 1994).

Clinically, sodium nitroprusside is used therapeutically to treat hypertension acutely. Its use is limited to acute hospital-based treatment because this nitric oxide releasing compound has a short lifetime of several minutes in blood (Palmer and Lasseter, *New Engl. J. Med.* 292: 294–297, 1975; Packer, Meller, Medine, Gorlin and Herman, *New Engl. J. Med.* 301: 1193–1197, 1979). The degradation of sodium nitroprusside is thought to arise through reductive processes taking place in the bloodstream. Even though it has been suggested that sulfhydryl groups attached to endothelial cells lining the vascular walls might initiate this reaction, other reductants such as glutathione or ascorbic acid may likewise contribute to its unusually short physiologic lifetime (Höbel, Kreye and Raithelhuber, *Herz.* 1: 130–136, 1976; Ivankovitch, Miletich and Tinker, *Int. Anesthesiol. Clin.* 16: 1–29, 1978; Kreye and Reske, *Arch. Pharmacol.* 320: 260–265, 1982). Based on this pharmacological behavior, the current clinical use of this drug requires that it is given continuously as an intravenous solution or it rapidly looses its efficacy concomitant with an increase in blood pressure to a hypertensive level.

Apparatuses and methods have been developed for delivering nitric oxide-releasing compounds and other drugs selectively and locally to a specific internal body site, e.g., for preventing restenosis after percutaneous transluminal coronary angioplasty. For instance, Cooke, Dzau and Gibbons (U.S. Pat. No. 5,428,070, 1995) described the use of orally administered L-arginine as a dietary supplement to enhance nitric oxide production by providing the substrate to nitric oxide synthase, the enzyme which metabolizes L-arginine to L-citrulline and nitric oxide. This would not be applicable to restenosis, since in this pathology, the endothelial cell levels of L-arginine are not diminished, but rather the specific isoform of nitric oxide synthase localized in endothelial cells is dysfunctional. Furthermore, even if levels of L-arginine were low, replacement therapy through supplementation of dietary L-arginine is an inappropriate treatment as cellular sources of L-arginine arise primarily from the reverse metabolism of L-citrulline to L-arginine (Sessa, Hecker, Mitchell and Vane, *Proc. Natl. Acad Sci. USA*, 87: 8607–8611, 1990).

U.S. Pat. No. 5,282,785 employs a drug delivery apparatus comprising a flexible catheter for insertion into an internal target area of the body and a drug delivery means connected to the catheter. In this version, the latter delivers the drug in a radially restricted manner and comprises (a) a drug delivery chamber at the distal end of the drug delivery apparatus, which has a selectively permeable outer membrane portion and circumferential lips adjacent to both the proximal and distal ends of the drug delivery system to minimize movement of a drug beyond a segment of internal tissue and a fluid delivery passageway extending from the chamber to the proximal end of the catheter; and (b) a non-permeable balloon affixed to and surrounding a portion of the chamber, which, when inflated, secures the chamber at the target area and radially restricts local delivery of the drug by providing intimate contact between balloon and a portion of the internal body tissue. The use of such an indwelling catheter device is limited to short term applications (usually no longer than 10–20 minutes), because it obstructs arterial blood flow. The apparatus also includes means of assisting the transport of the drug across the selectively permeable outer membrane with or without application of pressure.

Similarly, U.S. Pat. No. 5,286,254, also employs an apparatus, comprising a flexible catheter having a distal end and a proximal end and which is adapted for insertion into an internal area of a body; a drug delivery means having a fluid delivery passageway for delivering a drug to the distal end of the apparatus, an outer wall and a selectively permeable microporous outer membrane portion proximate to the distal end and an impermeable end to enhance delivery of the drug to the target area; and phoresis means for assisting the transport of the drug across the selectively permeable membrane.

These types of apparatuses described in U.S. Pat. Nos. 5,282,785 and 5,286,254 have several disadvantages. These catheter-based devices obstruct blood flow and therefore cannot stay in the circulation system very long. Therefore, long-term drug delivery is not possible using these systems. The presence of these items in the circulatory system promotes platelet deposition on the device.

U.S. Pat No. 5,370,614 describes the employment of a sheath coated with a matrix containing a drug and placed over the balloon of a balloon catheter. When placed at the point of treatment, the balloon is expanded and the sheath bursts from the pressure applied, releasing the drug as a bolus at the site of interest. Because restenosis occurs over a period of weeks and treatment would likely require the slow presentation of nitric oxide over an extended period of time, the approach of U.S. Pat. No. 5,370,614 cannot be applied to this disease condition.

U.S. Pat No. 5,470,307 describes the use of a coating to an apparatus to which a drug is covalently bonded to a substrate on the exterior surface of a catheter using a linker, which photolytically releases the agent upon exposure to a light source at an appropriate wavelength. The necessity to photolytically break a chemical bond in order to release nitric oxide has a clear disadvantage as there is no continued light source in the blood stream to cleave the linker molecule.

U.S. Pat. No. 5,278,192 describes the continual use of organic nitrites as vasodilator therapy on a chronic basis for 24 hours without developing tolerance. The necessity of organic nitrites to be metabolized by endothelial cells that have been made dysfunctional as the result of a disease state would not provide a continued local flux of nitric oxide to prevent restenosis and/or platelet aggregation at the affected site (Munson, "Principles of Pharmacology—Basic Concepts & Clinical Applications", pp. 482–483, 1995). Furthermore, regulating vascular tone is not the primary purpose of our invention and the local control of platelet aggregation and inhibition of intimal proliferation, leading to restenosis, altering systemic vascular tone through administration of either nitric oxide or a nitric oxide-releasing pro-drug is contraindicated.

U.S. Pat. No. 5,536,241 discloses a device for relaxing a smooth muscle of a hollow organ, the organ being a non-respiratory tract organ containing a non-blood biologic fluid and a source of nitric oxide, including nitric oxide gas and an NO-releasing compound such as sodium nitroprusside. This patent pertains to a device that does not come in contact with blood whereas our invention deals exclusively with the reactions of nitric oxide in blood, including inhibition of platelet aggregation and prevention of restenosis. In fact, the introduction of nitric oxide as a gas into the blood is contraindicated, since relaxation of the underlying smooth muscle could result in severe hypotension and death (see, Furchgott and Zawadzki, 1980, cited in the application).

U.S. Pat. No. 5,605,696 teaches that to prevent complications associated with insertion of a stent, such as restenosis, a polymer into which a therapeutic drug is incorporated therein, is coated onto this device. The pores of the coating have to be sufficiently large to allow the drug to diffuse from the coated stent into the blood stream of a human being. If the porosity of a coating produced by the selected polymer is not sufficient to allow the diffusion of the drug into the vasculature, a porosigen, such as lactose, is added to the polymer, thereby increasing the porosity sufficient to achieve release of the drug onto the blood stream. This drug delivery system allows the efficient efflux of the therapeutic drug from the polymer into the vasculature.

In contrast to the above cited patents, our invention relates to a different concept, viz., coating the surface of a foreign body, such as a stent, a catheter, a synthetic vascular graft, an implantable pump, a synthetic heart valve or other intravascular device or an extracorporeal device, such as the lumen (interior wall) of plastic tubing or the interior surfaces of pumps used for renal dialysis or cardiopulmonary bypass, with which the flowing blood of a living being comes in contact, with a polymeric coating containing a nitrosyl-containing organometallic compound, such as sodium nitroprusside (which is the pro-drug for nitric oxide), the drug employed in this invention, which is prevented by the coating from leaching into the blood stream but which permits the nitric oxide produced by the decomposition thereof to diffuse therefrom (for applications like renal dialysis or cardiopulmonary bypass)—with which blood or body tissue would come in contact.

SUMMARY OF THE INVENTION

In an article of manufacture aspect, this invention relates to an improvement in a device adapted for exposure to blood flowing in a living being and having a surface which is exposed to the blood and which is coated with a coating of a physiologically acceptable polymer which contains dissolved or dispersed therein a therapeutic drug, wherein the polymer coating is insoluble in the blood, inhibits diffusion of blood-borne reductants from entering the polymer coating and is gas permeable and the therapeutic drug dissolved or dispersed therein is an amount of nitrosyl-containing organometallic compound which at the body temperature of the living being slowly decomposes within the polymer coating when the device is exposed to the blood of the bloodstream of the living being and in so doing releases from the coating into the bloodstream of the living being nitric oxide at a rate effective to inhibit the platelet aggregation which could otherwise occur after the device is exposed to the blood.

In a process aspect, this invention relates to a method for the production of a device adapted for exposure to blood flowing in a living being and having a surface which is exposed to the blood which comprises the step of coating the surface with a coating of a physiologically acceptable polymer which contains dissolved or dispersed therein a therapeutic drug, wherein the polymer applied to the surface to form the coating is insoluble in the blood, inhibits diffusion of blood-borne reductants from entering the polymer coating and is gas permeable and the therapeutic drug dissolved or dispersed therein is an amount of nitrosyl-containing organometallic compound which at the body temperature of the living being slowly decomposes within the polymer coating when the device is exposed to the blood of the bloodstream of the living being and in so doing releases from the coating into the bloodstream of the living being nitric oxide at a rate effective to inhibit the platelet aggregation which could otherwise occur after the device is exposed to the blood.

In a method of use aspect, this invention relates to a method for inhibiting the aggregation of platelets from blood flowing in a living being from exposure of the blood to a foreign body by coating the surface of the foreign surface of a device adapted for exposure to blood flowing in a living being and having a surface which is exposed to the blood and which is coated with a coating of a physiologically acceptable polymer which contains dissolved or dispersed therein a therapeutic drug, wherein the polymer which -is applied to the surface to form the coating is insoluble in the blood, inhibits diffusion of blood-borne reductants from entering the polymer coating and is gas permeable and the therapeutic drug dissolved or dispersed therein is an amount of nitrosyl-containing organometallic compound which at the body temperature of the living being slowly decomposes within the polymer coating when the device is exposed to the blood of the bloodstream of the living being and in so doing releases from the coating into the bloodstream of the living being nitric oxide at a rate effective to inhibit the platelet aggregation which could otherwise occur after the device is exposed to the blood.

In a composition of matter aspect, this invention relates to a coating composition comprising (a) either an aqueous or an organic vehicle; (b) an injectable physiologically acceptable polymer dissolved or dispersed in the vehicle; and (c) a nitrosyl-containing organometallic compound, whether an ionic salt or a chelate, as defined herein which is precipitable from vehicle, e.g., by evaporation thereof to form a continuous coating containing the organometallic compound dissolved or dispersed therein.

DETAILED DESCRIPTION

This invention is based on the discovery that the aggregation of platelets in blood as a result of exposure of the blood to a foreign body or to the injured endothelium can be inhibited by a polymer coating on at least the surface(s) of the foreign body to which the circulating blood is exposed which contains an amount of a nitrosyl-containing organometallic compound, whether an ionic salt or a chelate, which is stable at room temperature but at body temperature and/or in the presence of ambient light while the foreign body is exposed to the blood releases from the coating a platelet-aggregation-inhibiting amount of nitric oxide, which amount produces a nitric oxide concentration locally at the surface of the foreign body which cannot safely be achieved by the systemic administration of a nitrosyl-containing organometallic compound, whether by intravenous or intra-arterial infusion.

Thus, this invention is useful for the inhibition of restenosis, a gradual re-occlusion of the blood vessel which usually occurs over a prolonged period of time, usually up to 6 weeks following trauma to the blood vessel, by providing a therapeutic concentration of NO proximate to the site of the trauma during that period of time.

In one article of manufacture aspect, this invention relates to intravascular medical devices such as synthetic (prosthetic) grafts, implantable pumps, heart valves and stents adapted for long term or permanent insertion into the lumen of a blood vessel, e.g., in conjunction with percutaneous transluminal angioplasty. In another aspect, the intravascular device is adapted for temporary insertion in a blood vessel, e.g., a balloon or catheter tip.

In yet another article of manufacture aspect, this invention relates to extravascular medical devices, such as plastic tubing or a membrane insert in the extravascular path of the blood stream of a living being undergoing a medical procedure requiring the cycling of the blood stream or a portion thereof outside the body of the living being, e.g., coronary artery bypass surgery or renal dialysis. In each of these aspects of this invention, a surface of the device which is in contact with the blood stream is coated with a polymer coating as described herein which contains an organometallic compound as described herein.

The method of this invention provides a method of inhibiting platelet aggregation, either in the form of a layer that builds up on a medical device that is permanently implanted in a blood vessel or that comes in contact with the circulating blood of a living being on a temporary basis or in the form of a detachable clot which, if it travels to the organs such as brain, lung, heart, kidney and liver, can be debilitating or have life-threatening sequelae. This method also applies to stents, indwelling catheters, other intravascular devices, either temporary or permanent, or to extracorporeal synthetic circuits for applications such as cardiopulmonary bypass or kidney dialysis.

This invention provides a novel method for the inhibition of restenosis, i.e., a gradual reocclusion of the blood vessel over a prolonged time period frequently occurring 4 to 6 weeks after surgery—by coating the surface of the foreign body, typically a stent, that contacts the blood with a polymer coating of this invention which contains dissolved or dispersed therein an amount of a nitrosyl-containing organometallic compound or a chelate which slowly decomposes within the polymer coating while the stent is in position in a vascularity of a living being and in so doing releases locally an amount of nitric oxide from the coating for a time period of up to 4 to 6 weeks or longer, which is effective to inhibit restenosis.

The polymeric coating employed in this invention contains a nitrosyl-containing organometallic compound, such as sodium nitroprusside, which is a pro-drug for the nitric oxide employed as the platelet aggregation inhibiting drug in this invention. Its porosity is sufficiently low to inhibit the diffusion of the nitrosyl-containing organometallic compound from the coating into the blood stream and also to inhibit blood-borne reductants from entering the polymer. The coating is, however, gas permeable and thus does not prevent the diffusion of nitric oxide from within the polymer coating into the blood stream.

Nitrosyl-containing organometallic compounds, whether ionic salts or chelates, employed in the composition of this invention are:

a. non-toxic, that is, substantially free from any significant toxic effects at their effective applied concentration;

b. substantially free of symptomology, that is, they do not produce significant symptoms detectable to the person treated at their effective applied concentration;

c. relatively stable at room temperature, away from light, i.e., once a nitrosyl-metal chelate is impregnated into a polymer and coated onto a stent or tubing or other device, nitric oxide is not released therefrom at a significant rate, e.g., during the preparation of the coating or its application to the stent, tubing or other device or thereafter, during self storage in a packaged container, is released at a rate, for example, less than 1% per month;

d. long lasting, that is, once a stent, tubing or other intra- or extravascular device bearing on the surface thereof a coating of the polymer impregnated with the nitrosyl-containing organometallic compound, whether an ionic salt or a chelate, comes in contact with blood or is inserted into a blood vessel, the duration of the delivery of nitric oxide can be adjusted by varying the concentration of the nitrosyl-containing organometallic compound in the polymer to conform to the clinical situation to be a matter of minutes, (e.g., 5–90 minutes in the case of a angioplasty balloon or catheter), hours (e.g., 1–4 hours in the case of hypothennic surgery blood circulation or cardiopulmonary bypass), hours to days (e.g., 3 hours to 3 days in the case of dialysis of blood passing though plastic tubing), or days to weeks (e.g., 4 to 6 weeks or longer in the case of a stent).

The Examples of a nitrosyl-containing organometallic compound employed in this invention, involve a compound of the formula $[MX_5NO]^{-2}Y^{+2}$ or $2Y^{+1}$ where M is a transition metal such as Fe, Co, Mn, Cu, Ni, Pt; X is a negatively a charged ion such as CN, Cl, Br, I, or chelates such as EDTA, DTPA, carbamates and dithiolates that at physiologic pH have negatively charged carboxylic and thiocarboxylic acid groups and Y is a positively charged salt.

A readily available example of the nitrosyl-containing organometallic chelates that can be employed in our invention is sodium nitroprusside, a compound in which an iron ion is complexed to five cyano groups and the sixth ligand position is occupied by a nitrosyl group.

Exposure of the polymer coating on the surface of a device of this invention containing such an organometallic compound encapsulated or dissolved therein to the blood steam of a living being releases nitric oxide from the coating in a controlled manner while retaining the other non-volatile decomposition products within the polymer coating. The enhanced stability of sodium nitroprusside in such a polymer coating, compared to its extremely short lifetime in such a blood stream, is the result of the inability of blood-containing reductants such as thiols and ascorbic acid to diffuse through the polymer coating and inactivate the sodium nitroprusside or rapidly decompose all of it, with concurrent rapid release of nitric oxide from the polymer coating, which thereby reduces or eliminates the long term benefits of prolonged release of nitric oxide achieved by protecting the sodium nitroprusside from direct contact with, the blood stream.

Other suitable complexing agents for the iron ion are ethylenediaminetetraacetic acid, EDTA; diethylenetriaminepentaacetic acid, DTPA and others of this class of chelates; 1,4,7,10-tetraazacyclododecane-N,N',N",N'"-tetraacetic acid, DOTA and trans-1,2-cyclohexylenediamine-N,N,N', N'-tetraacetic acid and others of this class of chelates; diethylthiocarbamate and similarly related carbamates; 1,2-dicyanoethylene-1,2-dithiolate and similarly related dithiolates.

This invention relates to methods, composition and articles of manufacture useful in the inhibition of platelet deposition either on a foreign body introduced surgically into a blood vessel or at vascular sites which have received treatment. Examples of such medical procedures include cardiopulmonary bypass during coronary artery bypass grafting ("CABG"), percutaneous transluminal angioplasty ("PTA") of peripheral arteries, arterial bypass surgery (either peripheral or coronary) using synthetic (prosthetic) vascular grafts, percutaneous transluminal coronary angioplasty ("PTCA") with stent implantation, and renal dialysis.

The reduction of platelet deposition has important implications for reducing the incidence of restenosis occurring following balloon angioplasty. By employing a polymer coating as defined herein to coat an implantable intravascular device such as a metal stent containing dissolved or dispersed therein a nitrosyl-containing organometallic compound in ionic salt or chelate form, nitric oxide can be locally delivered at any desired dose profile, which can be controlled by varying the concentration of the nitrosyl-containing organometallic compound, the specific polymer used to form or the nature and thickness of the coating, e.g., by employing multiple polymer coats containing varying concentrations of the organometallic compound. Thus, systemic nitric oxide toxicity, e.g., hypotension, can be prevented from occurring while at the same time achieving nitric oxide level locally at the site of the foreign body effective to inhibit platelet aggregation thereon or the formation of a detached or potentially detachable thrombus.

The nitrosyl-containing organometallic compound must be incorporated into a polymer coating whose porosity is sufficiently low to inhibit the diffusion of blood-borne reductants from entering the polymer and thereby inactivating the nitric oxide releasing compound of this invention yet is gas-permeable, i.e., has pores large enough to allow the passive diffusion of nitric oxide from inside the polymer coating into the bloodstream.

The coating on the foreign body preferably is from 0.1–1.0 mm thick and contains 1 micromole to 100 micromoles of the nitrosyl-containing organometallic compound per mm$^2$. Higher concentrations are desirable when the diffusion rate of the nitric oxide from the polymer is very slow or when it is desired that the release of the nitric oxide occurs over a prolonged period of time, e.g., more than 48 hours.

A wide variety of polymers can be used to encapsulate sodium nitroprusside and other nitrosyl-containing organometallic compounds, whether ionic salts or chelates, including both physiologically inert and biodegradable polymers and those which are only slowly soluble and those which are insoluble in blood for at least the period of time when any portion of the organometallic compound remains present therein. Insoluble polymers which are suitable are those which form a gas-permeable membrane coating around the foreign body so that the nitric oxide can migrate therefrom as it is produced. When the foreign body is inserted into the living being, it preferably is physiologically inert and, when permanently implanted, also biodegradable. Examples of biodegradable polymers which can be used as drug delivery systems include the natural polymers: collagen, albumin, casein, fibrin and gelatin (S. Bogdansky, in: *Biodegradable Polymers as Drug Delivery Systems*, ed. by M. Chasin and R. Langer, Marcel Dekker,. Inc. New York, pp. 231–259, 1990). Synthetic polymer systems include polylactide and polyglycodide (D. H. Lewis, in: *Biodegradable Polymers as Drug Delivery Systems*, ed. by M. Chasin and R. Langer, Marcel Dekker,. Inc. New York, pp. 1–42, 1990); polyvinyl alcohols (P. R. Byron and R. N. Dalby, *J. Pharm. Sci.* 76: 65–67, 1987); polyalkylene oxides and polyvinyl chlorides. Other suitable polymers include polyesters, polylactic anhydrides, celluloses, vinyl copolymers, homopolymers, acrylate, polycyanoacrylate, polyurethanes, silicone polymers and other types of polymers, such the dendrimers.

Characteristics of an "ideal" coating for a stent is one which can be applied to luminal or subluminal surfaces, does not cause a significant increase in stent wall thickness; is stable over time without desquamation; has a surface tension below 30 dyne/cm; has a smooth surface texture (<1 micron irregularities) has a negative or neutral surface charge; allows rapid endothelialization; permits timed elution of the nitric oxide; and delivers an effective concentration of nitric oxide locally to the site (S. R. Bailey, "Coating of Endovascular Stents" in: *Textbook of Interventional Cardiology*, ed. by E. J. Topol, Vol. 2, 2nd edition, W. B. Saunders, Philadelphia, pp. 754–765, 1994).

The desired coating can be formed by immersing the foreign body in a solution or colloidal dispersion of the selected polymer in either an aqueous or an organic vehicle containing dispersed therein the nitrosyl-containing organometallic compound, and then making the polymer insoluble, e.g., by changing the pH or the ionic strength, by or through evaporation of the solvent or by denaturing a proteinaceous polymer, so that a coating of the polymer with the nitrosyl-containing organometallic compound occluded therein deposits on the exposed surfaces of the foreign body. For example, a stent is placed in a tetrahydrofuran (THF) solution of polyvinyl chloride (PVC) in which the nitrosyl-containing organometallic compound is included therein, frequently a solid dispersed in the THF/PVC solution. The surface of the stent is thereby coated with a nitrosyl-containing organometallic compound dissolved in a solution of THF/PVC. Upon evaporation of the solution, the polymer encasing the nitric oxide releasing compound forms a film onto the surface of the stent.

The foreign body can be any medical device or product which has a surface that is exposed to the blood stream of a living being, which preferably is a human being, and is susceptible to or which promotes platelet aggregation. Intravascular devices and angioplasty surgery in general frequently promote platelet adhesion and aggregation. Placement of a stent into a living human being can also promote platelet aggregation and subsequent restenosis. Local delivery of nitric oxide can ameliorate these life-threatening conditions. Similarly, patients undergoing blood flow diversion outside the body, e.g., in conjunction with hypothermic surgery and dialysis of organs such as the kidney, have increased susceptibility to platelet aggregation due to a foreign body response resulting from the exposure of the blood to the plastic tubing used to transport the blood. A similar risk of foreign body response occurs in patients undergoing angiograms as a result of the insertion of plastic tubing into an artery. Therefore, anticoagulants are conventionally administered (with unavoidable associated risks) to suppress this response. When the interior of the tubing is coated with coating according to this invention, anticoagulants can be reduced or even eliminated entirely. Synthetic or reconstituted natural, e.g., from powdered bone and binder, bony structures can also trigger a foreign body response and therefore can benefit from a coating thereon according to this invention.

A preferred embodiment of the intravascular device aspect of this invention is a metal, e.g., stainless steel, or a polymeric intravascular stent which typically is implanted temporarily or permanently in a blood vessel after percutaneous transluminal coronary angioplasty.

The intravascular or extracorporeal devices of this invention can be constructed with pockets, grooves or other depressions in the surface of the device which can be filled with the polymer containing the organometallic compound. Alternatively, the nitrosyl-containing organometallic compound can first be deposited in the pockets, grooves or other depressions and the surface containing them and then coated with a polymer which does not contain the organometallic compound. Or a polymer coating containing the organometallic compound can first be formed on all of the surface(s) of the device which is exposed to the blood stream, or only a portion of that surface, and that polymer coating then covered with a protective polymer coating lacking the organometallic compound formed from the same polymer or a different polymer. Alternatively, the nitrosyl-containing organometallic compound can be incorporated into the structure of the device itself and the device then covered with a protective polymer coating which allows the diffusion of nitric oxide therethrough into the blood stream.

Preferred embodiments of the devices of this invention comprise one or more of the following:

a. The device is an intravascular device adapted for insertion into the bloodstream of the living being.

b. The intravascular device is in the form of a balloon, a catheter or a stent adapted to be inserted surgically into a blood vessel of a living being in conjunction with transluminal coronary angioplasty.

c. The intravascular device is a stent and the nitrosyl-containing organometallic compound is sodium nitroprusside.

d. The intravascular device has the nitrosyl-containing organometallic compound positioned within pockets, grooves or other depressions in the surface of the device and is covered with a coating of the physiologically acceptable polymer.

e. The coating containing the nitrosyl-containing organometallic compound is coated with a second coating of the same or different polymer that does not contain the organometallic compound.

f. The device is an extravascular device adapted to transport the blood of a patient undergoing coronary artery bypass surgery or renal dialysis.

g. The device is an extravascular device which comprises plastic tubing that is adapted to transport the blood and whose inner surface is coated with the polymer coating.

h. The extravascular device has the polymer coating on the surface of a membrane insert or on the inner surface of a section of the plastic tubing coated with the polymer coating, which is otherwise uncoated, which contacts the blood stream.

i. The extravascular device has sodium nitroprusside as the nitrosyl-containing organometallic compound.

The preferred methods for the production of a device of this invention and the preferred methods of using such a device also involve one or more of the above described preferred embodiments of this invention.

Figure 1A:
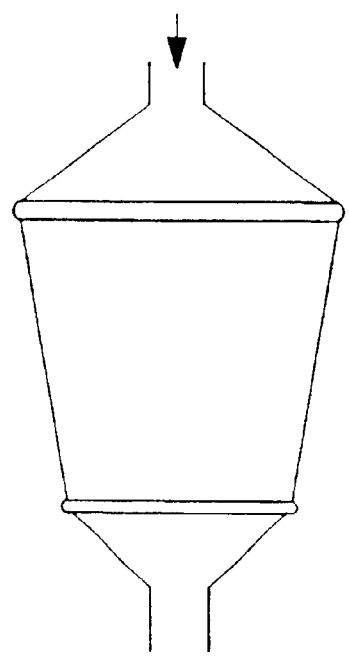
FIG. 1 shows the exterior, interior and cross sectional views of a platelet-inhibition element of this invention comprising a container adapted to be inserted in the blood flow loop of a patient undergoing renal dialysis or surgery involving extravascular transport of the blood stream of the patient and an accordion folded biologically inert synthetic polymer mesh insert for the container through which the blood of the patient must flow.

From the foregoing description, one skilled in the art can easily ascertain the essential characteristics of this invention, and without departing from the spirit and scope thereof, can make various changes and modifications of the invention to adapt it to various usages and conditions. The entire disclosures of all applications, patents and publications, cited above and below are incorporated by reference. The following preferred specific embodiments are, therefore, to be construed as merely illustrative and not limiting to the disclosure in anyway whatsoever.

EXAMPLE 1

Preparation of Nitric Oxide Delivery Systems. A 5% (w/w) of polyvinyl chloride (PVC, inherent viscosity 1.02, M.W. 40,000–85,000) solution was prepared by dissolving PVC (5 gm) in tetrahydrofuran (100 mL) at room temperature for 1 hour. After this PVC solution was prepared, sodium nitroprusside (1 gm SNP) was mixed with the PVC solution to give a SNP/PVC/THF suspension. Polyvinyl chloride tubing was coated with either PVC containing SNP or with PVC alone by allowing the solution of PVC containing the SNP or the corresponding solution containing only the PVC to flow through the tubing. After air drying the tubing, the coating process is repeated a number of times to obtain a coating containing the amount of SNP required to produce the desired flux of nitric oxide. Once the desired release rate of nitric oxide is achieved, a THF/PVC solution can be placed over the dried PVC containing SNP. In this manner, SNP is protected by an additional coating of PVC alone from blood elements, which rapidly inactivate SNP. Other surfaces, such as plastic Falcon tubes or glass coverslips, were coated in a similar manner.

EXAMPLE 2

Kinetics of Nitric Oxide Release from Plastic Surfaces. A plastic tube was coated with a solution of polyvinyl chloride (PVC, inherent viscosity 1.02, M.W. 40,000–85,000, solution was prepared by dissolving 5 gm of PVC in 100 mL tetrahydrofuran at room temperature for 1 hour) containing particulate sodium nitroprusside (<38 microns; 0.5% w/v). The solvent was removed by air drying to leave a polymer coating 0.1 to 1 mm thick. Nitrite accumulation using the Griess reagent in a sodium phosphate buffer was used as a measure of nitric oxide. Samples of the buffer was removed and analyzed daily, thereby ensuring that the determination of nitrite (a measure of nitric oxide) gave an accurate account of the daily release of nitric oxide. Samples (0.6 mL) were taken and added to freshly prepared Griess's reagent (0.4 mL of 0.1% N-(1-naphthyl)-ethylenediamine in water and 1% sulfanilamide in 5% phosphoric acid mixed 1:1). This reaction incubates for 15 minutes at room temperature and absorbance is recorded at 550 nm. Concentrations of nitrite were estimated by comparing absorbances at 550 nm against standard solutions of sodium nitrite prepared in the same buffer (Green, Wagner, Giogowski, Skipper, Wishnok and Tannebaum, *Anal. Biochem.* 126: 131–138, 1982). The first few days of nitric oxide release from the polymer into the phosphate buffer at 37° C. was high, achieving a maximal concentration of approximately 35 micromolar of nitric oxide by day 3. At this point, the concentration of nitric oxide decreased slowly, achieving, by day 35, an equilibrium flux of 8 micromolar of nitric oxide. This rate of nitric oxide release remained constant for 52 days, when the experiment was terminated. These results demonstrate that sodium nitroprusside incorporated into a PVC coating can release nitric oxide into a phosphate buffer at 37° C. in the absence of blood-containing reductants.

EXAMPLE 3

An in vivo experiment was employed to evaluate the ability of a polymer coating, produced by casting a solution of polyvinyl chloride (PVC, inherent viscosity 1.02, M.W. 40,000–85,000, solution was prepared by dissolving 5 gm of PVC in 100 mL tetrahydrofuran at room temperature for 1 hour) containing particulate (<38 microns; 0.5% w/v) sodium nitroprusside dispersed therein onto the lumen of PVC tubing and air drying to remove the solvent, to inhibit platelet aggregation. An artificial A-V fistula was created between the femoral artery and vein of a pig with PVC- and PVC/SNP-coated tubing connected in parallel. The flow rate in the A-V fistula tubing was adjusted to 80 mL/min. Blood samples were taken for ADP-induced platelet aggregation and measurement of serum nitrite concentrations at locations close to the femoral artery and at the distal end of the PVC-coated and PVC/SNP-coated tubing. Samples were collected every hour after establishing the artificial A-V fistula and 20 minutes after the disconnection of the fistula. After the blood pressure was stabilized at about 75 mm Hg, the flow through the tubing was begun. One hour after establishing the A-V fistula, blood sampled from the PVC/SNP-coated tubing showed 69% inhibition of platelet aggregation as compared to 24% inhibition for blood sampled from the uncoated control tubing. Of interest is the finding that even after 4 hours of flow through the PVC/SNP-coated tubing during which platelet aggregation remained markedly inhibited (platelet inhibition of the PVC/SNP-coated tubing at over 200% of control), blood pressure was unchanged, remaining at about 75 mm Hg. It is clear from these data that a slow release of nitric oxide through the PVC polymer inhibits platelet aggregation as compared to the control, PVC alone.

Biologic Assay for Nitric Oxide—Platelet Aggregation. Aggregation of human platelets was measured optically with a four-channel platelet aggregometer (Model 560-Ca, Chromolog, Havertown, Pa.). Venous blood was collected in a citrated tube, centrifuged at 250×g to isolate platelet rich plasma (PRP, platelet count with approximately 300,000/mL). Platelet aggregation was induced by ADP (10 micromolar, final concentration).

EXAMPLE 4

The fact that selective diffusion is achievable by our invention was verified by the following experiments, which were designed to test the relative diffusiveness of sodium nitroprusside (a readily available example of the general class of nitrosyl-containing organometallic compounds employed in our invention) and nitric oxide through a polyvinyl chloride coating.

A solution of sodium nitroprusside (10 mM in sodium phosphate buffer, pH 7.4) was placed within a PVC tube (the inner tube) and sealed. A second larger PVC tube (the outer tube) filled with only sodium phosphate buffer at pH 7.4 was fitted around the inner tube containing the solution of SNP and it also was sealed. This device was placed on a laboratory bench and maintained at ambient conditions for 3 days. At this point, the contents of each of the sealed tubes were analyzed.

We analyzed for SNP in each tube. The analysis showed that the inner tube contained residual SNP and the non-volatile components of the portion of the SNP which had decomposed, as shown by the UV-visible spectrum analysis for SNP in the phosphate buffer. In contrast, the contents of the outer tube did not exhibit any UV-visible spectrum absorption. These findings demonstrate that the sodium nitroprusside did not diffuse through the wall of the inner tube into the outer tube. We also analyzed for nitric oxide to determine whether the nitric oxide produced by the decomposition of the sodium nitroprusside in the solution in the inner tube had diffused into the outer tube. We did so by measuring the amount of nitrite present, which provides an estimate of nitric oxide content, using the method of Green, et al., (Anal. Biochem. 126: 131–138, 1982). This analysis demonstrated that 80 micromolar nitrite had accumulated in the outer tube, thus confirming that nitric oxide had diffused from the inner tubing into the outer tubing, whereas the SNP had not.

Taken together, these experiments proved that the sodium nitroprusside in the inner tube had decomposed and produced nitric oxide and the porosity of the coating was sufficiently small to prevent sodium nitroprusside from migrating therefrom and collecting in the outer tube but was gas permeable and therefore did not prevent the nitric oxide generated in the inner tube from diffusing through the wall thereof into the buffer solution in the outer tube.

EXAMPLE 5

Figure 1B:
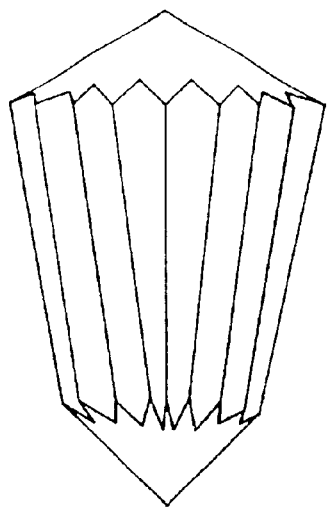
Figure 1C:
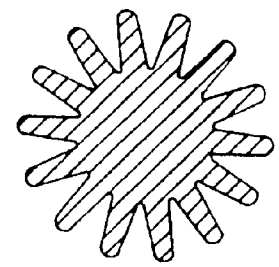

Construction of a platelet-inhibition element. A platelet-inhibition element (FIG. 1) may be constructed by placing a large surface area filter into a cylindrical device which then can be inserted into an extracorporeal blood pathway during procedures such as cardiopulmonary bypass surgery and renal dialysis. The membrane and/or the internal surfaces of the cylinder can be coated with a polymer into which the nitrosyl-containing organometallic compound is incorporated therein. A preparation of this nitric oxide delivery system is as follows: A 5% (w/w) of polyvinyl chloride (PVC, inherent viscosity 1.02, M.W. 40,000–85,000) solution is prepared by dissolving PVC (5 gm) in tetrahydrofuran (100 mL) at room temperature for 1 hour. After this PVC solution is prepared, sodium nitroprusside (1 gm SNP) is mixed with the PVC/THF solution to give a SNP/PVC/THF suspension. The membrane and/or the internal surfaces of the platelet-inhibition element are coated with PVC containing SNP by allowing the corresponding solution to flow through the device. After air drying the device, the coating process can be repeated a number of times to obtain the desired flux of nitric oxide.

EXAMPLE 6

Figure 2A:
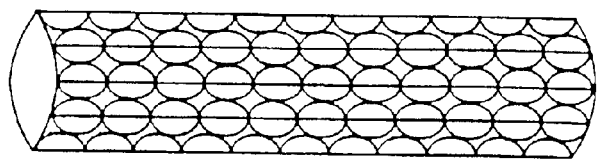
FIG. 2 shows the side view (FIG. 2A) and cross sectional top view of a stent (FIG. 2B) of this invention which contains grooves in the inner walls thereof for deposition of the organometallic compound.
FIG. 2C is an end view of the cross sectional section of the stent with the organometallic compound deposited in the grooves and covered with the polymer coating of this invention.
Figure 2B:
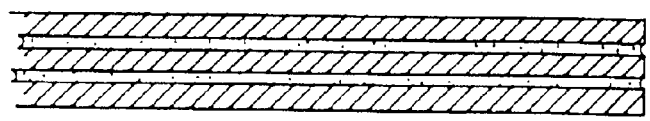
Figure 2C:

Construction of a drug-delivery stent. The stent (FIG. 2) is constructed of metal in which grooves are created along its length into which a nitrosyl-containing organometallic compound can be placed. This surface in which the nitrosyl-containing organometallic compound is placed is then covered with a physiologically acceptable polymer. A preparation of this nitric oxide delivery system is as follows: First sodium nitroprusside (1 gm SNP) is ground, and the resulting powder placed in the grooves of the stent. Then a 5% (w/w) of polyvinyl chloride (PVC, inherent viscosity 1.02, M.W. 40,000–85,000) solution is prepared by dissolving PVC (5 gm) in tetrahydrofuran (100 mL) at room temperature for 1 hour. This solution is then coated over the grooves on the stent containing the sodium nitroprusside. After air drying the drug delivery stent, the coating process can be repeated a number of times to obtain the desired flux of nitric oxide. In this manner, SNP is protected from blood elements, which rapidly inactivate SNP, by the coating of PVC alone.

What is claimed is:

1. A medical device comprising a surface coated with a physiologically acceptable polymer which contains dissolved or dispersed therein a nitrosyl-containing organometallic compound, wherein the polymer coating is insoluble when in contact with blood for at least a period of time when any portion of the organometallic compound remains present therein, inhibits diffusion of reductants into the coating, inhibits the release of the nitrosyl-containing organometallic compound and releases nitric oxide when the device is inset in contact with in blood.

2. The device according to claim 1, wherein the coating is from about 0.1 mm to about 1.0 mm thick.

3. The device according to claim 1, wherein the coating contains from about 1 mmole/mm$^2$ to about 100 mmole/mm$^2$ of the nitrosyl containing organometallic compound.

4. The device according to claim 1, wherein the device is an intravascular device adapted for insertion into the blood stream.

5. The device according to claim 4, in the form of a balloon, a catheter or a stent.

6. The device according to claim 1, wherein the device is adapted to be inserted surgically into a blood vessel in conjunction with transluminal coronary angioplasty, a prosthetic vascular graft, implantable pump or heart valve.

7. The device according to claim 1, wherein the nitrosyl-containing organometallic compound is sodium nitroprusside.

8. The device according to claim 1, wherein the coating containing the nitrosyl-containing organometallic compound is coated with a second coating of the same or a different polymer that does not contain the nitric oxide releasing organometallic compound.

9. The device according to claim 1, wherein the device comprises plastic tubing and surfaces, polytetrafluorethylene tubing and surfaces or a metal surface.

10. The device according to claim 1, wherein the coating is applied to an inner surface of the device.

11. The device according to claims 10, wherein the device is adapted to transport the blood of a patient undergoing coronary bypass or renal dialysis.

12. The device according to claim 10, wherein the coating is applied to only a section of the inner surface of the device.

13. The device according to claim 1, wherein the coating is on a separate insert in an extravascular tube.

14. A medical device comprising a surface coated with a physiologically acceptable polymer coating which encapsulates a nitrosyl-containing organometallic compound wherein the polymer coating is insoluble when in contact with blood for at least a period of time when any portion of the organometallic compound remains present therein, inhibits the release of the nitrosyl-containing organometallic compound and is gas permeable.

15. The device according to claim 14, wherein the polymer inhibits diffusion of reductants into the coating.

16. The device according to claim 14, wherein the coating allows nitric oxide produced from the nitrosyl containing organometallic compound to migrate from the coating.

17. The device according to claim 14, wherein the device is adapted to be permanently implanted.

18. The device according to claim 14, wherein the polymer coating comprises a biodegradable polymer.

19. The device according to claim 14, wherein the polymer coating comprises a synthetic polymer.

20. The device according to claim 19, wherein the synthetic polymer is selected from the group consisting of polyalkylene oxides, polyvinyl chloride, polyester, polylactic anhydride, cellulose, vinyl polymers, acrylates, polycyanoacrylates, polyurethanes and silicone polymers.

21. The device according to claim 14, wherein the polymer has a surface tension below about 30 dyne/cm.

22. The device according to claim 14, wherein the coating has a smooth texture.

23. The device according to claim 14, wherein irregularities in the coating surface are less than 1 micron in size.

24. The device according to claim 14, wherein the coating surface is neutral or has a negative charge.

25. The device according to claim 14, wherein the coating allows rapid endothelialization.

26. The device according to claim 14, wherein the coating permits timed elution of nitric oxide.

27. The device according to claim 14, wherein the coating elutes a concentration of nitric oxide effective to prevent platelet aggregation.

28. The device according to claim 14, wherein the coating allows elution a concentration of nitric oxide effective to prevent restenosis.

* * * * *